United States Patent
Price et al.

(10) Patent No.: US 11,951,225 B2
(45) Date of Patent: Apr. 9, 2024

(54) MEDICAL INSTRUMENT STERILIZATION CASE TRACKING

(71) Applicant: DePuy Synthes Products, Inc., Raynham, MA (US)

(72) Inventors: Avery Price, Reading, PA (US); Rene Haag, Berwyn, PA (US); Sriram Raghunathan, Chennai (IN); Daniel Essafi, Manchester (GB)

(73) Assignee: DePuy Synthes Products, Inc., Raynham, MA (US)

( * ) Notice: Subject to any disclaimer, the term of this patent is extended or adjusted under 35 U.S.C. 154(b) by 508 days.

(21) Appl. No.: 16/728,511

(22) Filed: Dec. 27, 2019

(65) Prior Publication Data

US 2021/0113729 A1    Apr. 22, 2021

(30) Foreign Application Priority Data

Oct. 22, 2019    (IN) .............................. 201911042910

(51) Int. Cl.
*A61L 2/28*    (2006.01)
*A61B 34/20*    (2016.01)
(Continued)

(52) U.S. Cl.
CPC ................ *A61L 2/28* (2013.01); *A61B 34/20* (2016.02); *A61L 2/07* (2013.01); *A61L 2/24* (2013.01);
(Continued)

(58) Field of Classification Search
CPC ..... A61L 2/28; A61L 2/07; A61L 2/24; A61L 2202/122; A61L 2202/182; A61L 2202/24;
(Continued)

(56) References Cited

U.S. PATENT DOCUMENTS 5,696,686 A * 12/1997 Sanka ........................ A61L 2/24
700/110
2006/0192679 A1* 8/2006 Buckley .............. G01F 23/2885
340/618
(Continued)

FOREIGN PATENT DOCUMENTS

KR    200324130 Y1 * 8/2003    ............... A61L 2/24
WO    WO-03074093 A2 * 9/2003    ............. A61L 12/04
(Continued)

OTHER PUBLICATIONS

Bimetallic strip, Wikipedia, https://en.wikipedia.org/wiki/Bimetallic_strip, web-archive capture from Sep. 4, 2019, accessed on Dec. 22, 2020 from https://web.archive.org/web/20190904174015/https://en.wikipedia.org/wiki/Bimetallic_strip, 3 pages.
(Continued)

*Primary Examiner* — Regina M Yoo
(74) *Attorney, Agent, or Firm* — BakerHostetler

(57) ABSTRACT

A battery-powered tracking component may be attached to a sterilization case. The tracking component may collect, store and transmit usage information associated with the sterilization case. The supplying of power to the tracking component may be temporarily stopped during autoclave processes. As the high temperatures and pressurized steam of autoclave processes may drain an active battery, the lifespan of the battery may be elongated by deactivating the battery during the autoclave processes. A temperature sensor may detect when the temperature of the sterilization case rises above a threshold indicating a start of the autoclave process, and when the temperature of the sterilization case falls below a threshold indicating an end of the autoclave process. The usage information may include a count of autoclave processes and durations of time periods between autoclave processes. The usage information may be used to
(Continued)

determine times at which autoclave processes are performed.

4 Claims, 4 Drawing Sheets

(51) Int. Cl.
*A61L 2/07* (2006.01)
*A61L 2/24* (2006.01)
(52) U.S. Cl.
CPC . *A61B 2562/0271* (2013.01); *A61L 2202/122* (2013.01); *A61L 2202/182* (2013.01); *A61L 2202/24* (2013.01)
(58) Field of Classification Search
CPC ... A61L 2/04; A61B 34/20; A61B 2562/0271; A61B 2017/00084; A61B 2017/00734; A61B 2034/2046; A61B 2090/0803; A61B 2090/0813; A61B 90/98
See application file for complete search history.

(56) References Cited

U.S. PATENT DOCUMENTS

| | | | | |
|---|---|---|---|---|
| 2007/0094303 | A1* | 4/2007 | Zwingenberger | G06Q 10/087 |
| 2009/0064430 | A1* | 3/2009 | Jimenez | A46B 15/0008 |
| | | | | 15/22.1 |
| 2009/0292167 | A1* | 11/2009 | Kimoto | A61B 5/073 |
| | | | | 600/109 |
| 2013/0277574 | A1* | 10/2013 | Dayton | A61L 2/10 |
| | | | | 250/455.11 |
| 2015/0217007 | A1* | 8/2015 | Smith | A61L 2/06 |
| | | | | 422/292 |
| 2016/0193374 | A1* | 7/2016 | Sarphati | A61L 2/24 |
| | | | | 422/114 |
| 2017/0224859 | A1 | 8/2017 | Broninx et al. | |
| 2018/0078331 | A1* | 3/2018 | Khalife | A61B 90/90 |
| 2019/0013830 | A1 | 1/2019 | Hoglund et al. | |
| 2020/0237939 | A1* | 7/2020 | Henniges | A61L 2/07 |
| 2021/0215551 | A1* | 7/2021 | Fonk | G01K 3/04 |

FOREIGN PATENT DOCUMENTS

| | | | | |
|---|---|---|---|---|
| WO | WO-2014091448 A1 * | 6/2014 | | A61L 2/26 |
| WO | WO-2017016958 A1 * | 2/2017 | | A61B 90/08 |
| WO | 2017/083992 A1 | 5/2017 | | |
| WO | WO-2019096850 A1 * | 5/2019 | | A61L 2/26 |

OTHER PUBLICATIONS

Wikipedia—Electronic Oscillator, https://en.wikipedia.org/wiki/Electronic_oscillator, web-archive capture from Aug. 11, 2019, accessed on Feb. 21, 2023 from https://web.archive.org/web/20190811111900/https://en.wikipedia.org/wiki/Electronic_oscillator.
Wikipedia—Electronic Oscillator, https://en.wikipedia.org/wiki/Electronic_oscillator, web-archive capture from Oct. 4, 2019, accessed on Feb. 21, 2023 from https://web.archive.org/web/20191004234716/https://en.wikipedia.org/wiki/Electronic_oscillator.

* cited by examiner

MEDICAL INSTRUMENT STERILIZATION CASE TRACKING

BACKGROUND

It is important for hospitals and other medical facilities to track the use of medical instruments, such as surgical instruments used in surgery. Some example medical instruments may include screws, forceps, scalpel blades, retractors, and other medical instruments. In some examples, hospitals may attempt to track the locations and times at which medical instruments are used and stored. This may assist in allowing a determination of an appropriate cost for use of the medical instruments. Medical instruments are often stored in a sterilization case, which is used to store and sterilize the medical instruments after use in a surgical or other medical procedure. Some existing techniques for tracking the use of medical instruments may include having an employee operate a scanner to scan a bar code or other identifier of the medical instruments and/or the case in which they are stored, but this may require extra steps that reduce efficiency and complicate procedures.

Medical instruments may be sterilized in a sterilization case by implementing an autoclave sterilization process, in which the medical instruments and the sterilization case may be subjected to high temperatures and pressurized steam, which may damage or degrade electronic components. For example, exposing an active battery (i.e., a battery that is in the act of supplying power to another component) to the high temperatures and pressurized steam of an autoclave process may drain the battery more quickly than normal temperature and pressure conditions.

SUMMARY

Techniques for medical instrument sterilization case tracking are described herein. Medical instruments, such as surgical instruments used in surgery, may be stored in a sterilization case, which is used to store and sterilize the medical instruments after use in a surgical or other medical procedure. Some example medical instruments may include screws, forceps, scalpel blades, retractors, and other medical instruments. Medical instruments may be sterilized in the sterilization case by implementing an autoclave sterilization process, in which the medical instruments and the sterilization case may be subjected to high temperatures and pressurized steam.

A tracking component may be attached to the sterilization case. The tracking component may be battery-powered and may collect, store and transmit usage information associated with the sterilization case. In some examples, the usage information may include information such as a count of autoclave processes that are performed on the sterilization case, durations of time periods between autoclave processes, and a duration of a time period between a most recent autoclave process and a time at which the usage information is obtained from the tracking component by an external device. The usage information may be transmitted periodically, such as at repeating intervals, for example every few minutes while the tracking component is powered-on. In some examples, the usage information may be transmitted using a short-range wireless communications protocol. The usage information may be transmitted from the tracking component to an external device, such as a smart phone or other computing device. The external device may include location-based services, such as global positioning system (GPS) services, which may be used to determine the location of the external device. In some examples, because the tracking component and the external device may communicate via a short-range wireless communications protocol, the location of the external device may be assumed to be identical or almost identical to the location of the sterilization case. The location of the sterilization case at the time that it transmits data to the external device may therefore be determined based on the location of the external device. In some examples, after being received by the external device, the usage information may be re-transmitted to other components, such as cloud-based or server-based services, for further computation and analysis.

As described above, the tracking component may be battery-powered. The battery may be connected to the tracking component to supply power to the tracking component. In some examples, the battery may also be temporarily disconnected from the tracking component to temporarily stop the supply of power to the tracking component. In some examples, the supplying of power to the tracking component may be temporarily stopped (e.g., interrupted) during autoclave processes of the sterilization case, such as by disconnecting the battery from the tracking component or otherwise stopping the supply of power to the tracking component. As the high temperatures and pressurized steam of autoclave processes may drain an active battery, the lifespan of the battery may be elongated by deactivating the battery during the autoclave processes. It is noted, however, that, because the tracking component may be powered-off during autoclave processes, the tracking component may be unable to track the exact lengths of the autoclave processes. In some examples, the starting and ending of an autoclave process may be determined by a temperature sensor, such may be included in a hardware temperature switch or other switching component, that may also be attached to the sterilization case. Specifically, the temperature sensor may detect when the temperature of the sterilization case rises above a particular temperature threshold indicating a start of the autoclave process, and the switching component may then disconnect the battery from the tracking component or otherwise stop the supply of power to the tracking component. Additionally, the temperature sensor may detect when the temperature of the sterilization case falls below a particular temperature threshold indicating an end of the autoclave process, and the switching component may then reconnect the battery to the tracking component or otherwise resume the supply of power to the tracking component.

In some examples, the usage information may be used to determine times at which one or more autoclave processes are performed. For example, the usage information may include a first duration of a first time period between a completion of a most recent autoclave process and a time at which the usage information is obtained from the tracking component by an external device. In some examples, the time at which the most recent autoclave process is completed may be determined by subtracting the first duration of the first time period from the time at which the usage information is obtained. Also, in some examples, because the tracking component may be powered-off during autoclave processes, the exact times of the autoclave processes may be unknown and may instead be estimated, such based on average durations of autoclave processes that may be measured over time. An estimated autoclave process duration may then be used to estimate times of other autoclave processes preceding the most recent autoclave process. For example, a time of a completion of an autoclave process may be determined by subtracting, from the time at which the usage information is obtained, the estimated autoclave process duration for each intervening autoclave process and the measured time durations that are tracked before each intervening autoclave process and after the most recent autoclave process.

BRIEF DESCRIPTION OF THE DRAWINGS

The foregoing summary, as well as the following detailed description of the preferred embodiments of the application, will be better understood when read in conjunction with the appended drawings. For the purposes of illustrating the methods and/or techniques of orthopedic fixation with imagery analysis, there are shown in the drawings preferred embodiments. It should be understood, however, that the instant application is not limited to the precise arrangements and/or instrumentalities illustrated in the drawings, in which.

DETAILED DESCRIPTION

Figure 1:
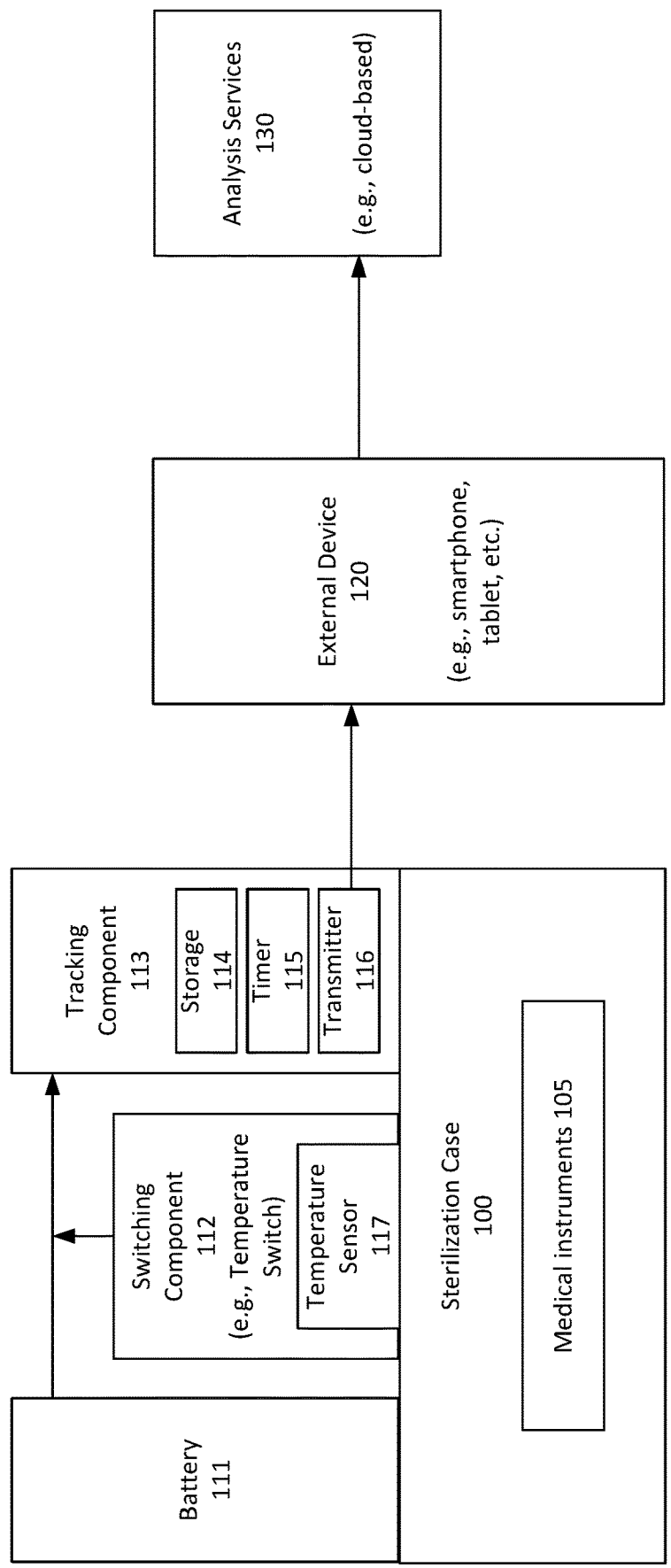
FIG. 1 is a diagram of an example medical instrument sterilization case tracking system that may be used in accordance with the present disclosure.

Techniques for medical instrument sterilization case tracking are described herein. Referring now to FIG. 1, an example medical instrument sterilization case tracking system will now be described in detail. As shown in FIG. 1, medical instruments 105, such as surgical instruments used in surgery, may be stored in a sterilization case 100, which is used to store and sterilize the medical instruments 105 after use in a surgical or other medical procedure. Some example medical instruments 105 may include screws, forceps, scalpel blades, retractors, and other medical instruments. Medical instruments 105 may be sterilized in the sterilization case by implementing an autoclave sterilization process, in which the medical instruments and the sterilization case may be subjected to high temperatures and pressurized steam.

As also shown in FIG. 1, a tracking component 113 is attached to the sterilization case 100. The tracking component 113 is powered by a battery 111. The tracking components 113 collects, stores and transmits usage information associated with the sterilization case 100. In some examples, the usage information may include information such as a count of autoclave processes that are performed on the sterilization case, durations of time periods between autoclave processes (e.g., durations of time periods between consecutive autoclave processes), and a duration of a time period between a most recent autoclave process and a time at which the usage information is obtained from the tracking component by an external device 120. The term consecutive autoclave processes, as used herein, refers to autoclave processes that are performed successively on the same sterilization case with no intervening autoclave processes—although it is understood that there will be a time period between the consecutive autoclave processes. The tracking component 113 includes a timer 115 for counting or measuring time intervals included in the usage information, such as counting of seconds or other time intervals when the tracking component 113 is powered-on, for example time intervals between consecutive autoclave processes and/or a time interval after a most recent autoclave process. In some examples, the tracking component 113 and/or timer 115 may include a crystal oscillator or other electronic oscillator circuit, such as to enable tracking of time. The tracking component 113 may include one or more integrated circuits, such as one or more integrated circuit chips, and may include memory that stores processor-readable and/or machine-readable instructions and a processor for executing those stored instructions. The stored instructions may include instructions for performing any or all of the acts described herein as being performed by the tracking component 113. Upon being executed by the tracking component 113 (e.g., by a processor of the tracking component 113), the stored instructions may cause the tracking component 113 to perform those acts. In the example of FIG. 1, the tracking component 113 includes storage 114, such as memory, for example for storing the instructions described above as well as autoclave process quantity counts, timing information, or other usage information. In some examples, the storage 114 may include built-in flash memory, which may be more heat resistant than some other types of memory, such as random-access memory (RAM).

The tracking component 113 includes a transmitter 116 that transmits the tracked usage information. The usage information may be transmitted periodically, such as at repeating intervals, for example every few minutes while the tracking component 113 is powered-on. In some examples, the usage information may be transmitted using a short-range wireless communications protocol, such as the BLUETOOTH® protocol. The usage information may be transmitted from the tracking component 113 to an external device 120, such as a smart phone, tablet or other computing device. The external device may include location-based services, such as global positioning system (GPS) services, which may be used to determine the location of the external device 120. In some examples, because the tracking component 113 and the external device 120 may communicate via a short-range wireless communications protocol, the location of the external device 120 may be assumed to be identical or almost identical to the location of the sterilization case 100. The location of the sterilization case 100 at the time that it transmits data to the external device 120 may therefore be determined based on the location of the external device 120 at that same time. For example, the location of the sterilization case 100 at the time that it transmits data to the external device 120 may be determined to be identical or almost identical to the location of the external device 120 at that same time. In some examples, after being received by the external device, the usage information may be re-transmitted to analysis services 130, such as cloud-based or server-based services, for further computation and analysis.

As described above, the tracking component 113 may be powered by battery 111. The battery 111 may be attached to the sterilization case and may be connected to the tracking component to supply power to the tracking component 113. In some examples, the battery 111 may also be temporarily disconnected from the tracking component 113 to temporarily stop the supply of power to the tracking component 113. In some examples, the supplying of power to the tracking component 113 may be temporarily stopped (e.g., interrupted) during autoclave processes of the sterilization case 100, such as by disconnecting the battery 111 from the tracking component 113 or otherwise stopping the supply of power to the tracking component 113. As the high temperatures and pressurized steam of autoclave processes may drain an active battery, the lifespan of the battery 111 may be elongated by deactivating the battery 111 during the autoclave processes. It is noted, however, that, because the tracking component 113 may be powered-off during autoclave processes, the tracking component 113 may be unable to track the exact lengths of the autoclave processes. In some examples, the starting and ending of an autoclave process may be determined by a switching component 112, that is also attached to the sterilization case 100.

The switching component 112 may deactivate and reactivate the battery 111 based on the starting and ending of an autoclave process. In some examples, the switching component 112 may be a hardware temperature switch that connects and disconnects the battery 111 to and from the tracking component 103 based on the temperature of the sterilization case 100. Specifically, the switching component 112 may include a temperature sensor 117, which may detect when the temperature of the sterilization case rises above a particular temperature threshold indicating a start of the autoclave process, and the switching component 112 may then disconnect the battery 111 from the tracking component 113 or otherwise stop the supply of power to the tracking component 113. Additionally, the temperature sensor 117 may detect when the temperature of the sterilization case falls below a particular temperature threshold indicating an end of the autoclave process, and the switching component 112 may then reconnect the battery 111 to the tracking component 113 or otherwise resume the supply of power to tracking component 113. In some examples, the temperature sensor 117 and/or switching component 112 may include a creep action thermostat and/or thermal protector, such as may include conductive bimetal construction. Also, in some examples, the switching component 112 may be calibrated to open or curl enough to break contact at different temperatures. For example, in some cases, the switching component 112 may be calibrated to open or curl enough to break contact or otherwise disconnect the battery when the switching component 112 detects an increase to a temperature that is indicative of a start of an autoclave process. In one specific example, an increase to a temperature of one hundred degrees (Fahrenheit) may be determined to be indicative of a start of an autoclave process. However, other temperatures may also be used. Additionally, in some examples, the switching component may be calibrated to close or resume contact or otherwise reconnect the battery when the switching component detects a decrease to a temperature that is indicative of an end of autoclave process, such as a decrease to one hundred degrees (Fahrenheit) or below. The term detect, as used herein, refers to a component sensing or otherwise being exposed to a temperature or other condition that causes, or results in, the component performing an action (and/or assuming a state) based on the condition. For example, the switching component 112 detecting a temperature that indicates a start of autoclave process refers to the switching component 112 sensing or otherwise being exposed to a temperature that causes the switching component to perform an action (and/or assume a state) based on that temperature (e.g., curling or otherwise disconnecting the battery from the tracking component). There is no requirement that the switching component 112 must be aware of a temperature or other condition that it detects. For example, there is also no requirement that the switching component 112 must display a temperature reading or otherwise report or keep a record of a condition that it detects.

Figure 2:
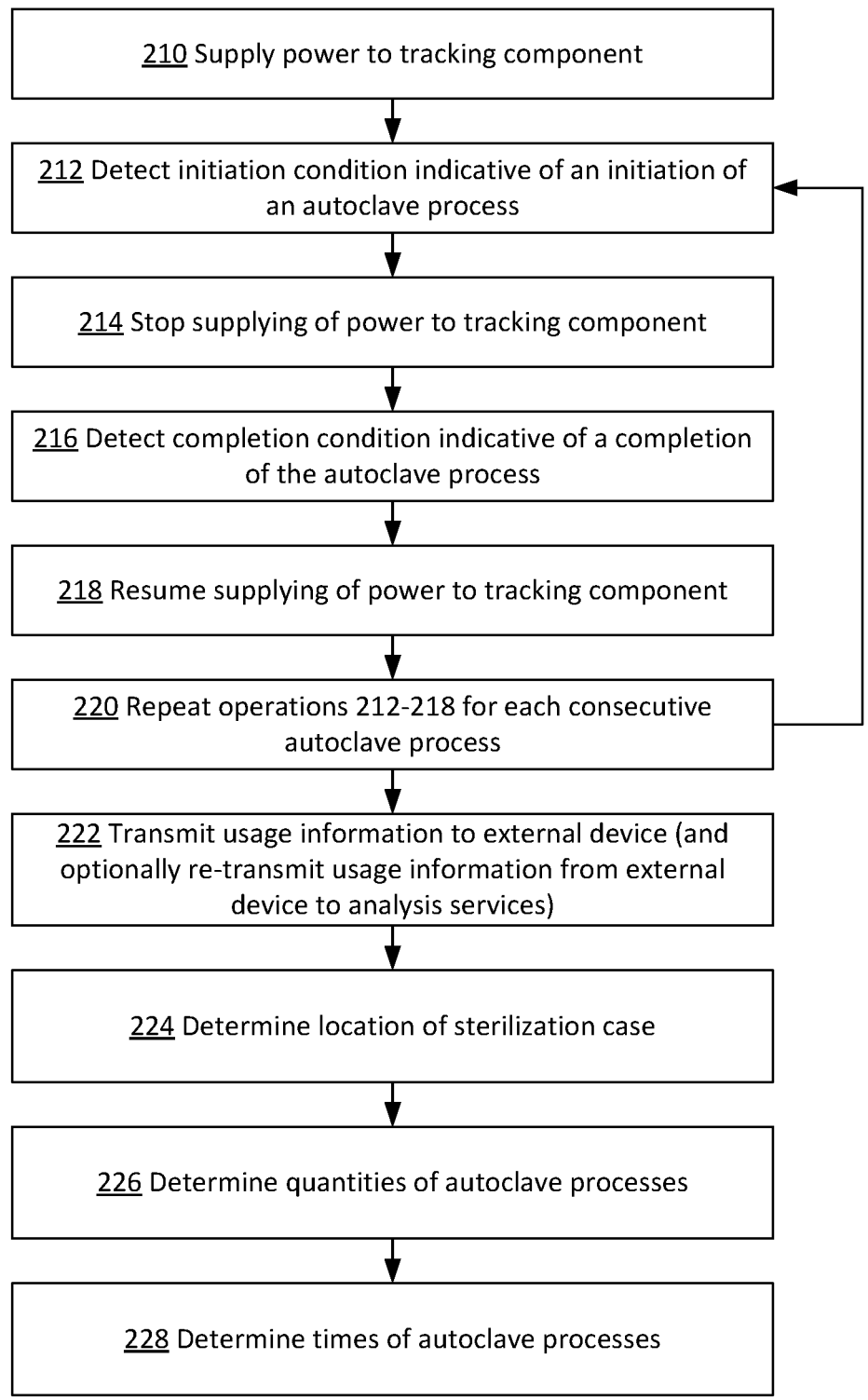
FIG. 2 is a flow diagram illustrating an example medical instrument sterilization case tracking process that may be used in accordance with the present disclosure.

Referring now to FIG. 2, an example medical instrument sterilization case tracking process will now be described in detail. The process of FIG. 2 is initiated at operation 210, at which power is supplied to a tracking component that is battery-powered and that collects, stores, and transmits usage information associated with a sterilization case in which medical instruments are sterilized. As described above, the supplying of power to the tracking component may be achieved by connecting a battery to the tracking component and allowing power to flow from the battery to the tracking component.

At operation 212, an initiation condition is detected that is indicative of an initiation of an autoclave process that sterilizes medical instruments in the sterilization case. In some examples, the initiation condition may be an increase in the temperature of the sterilization case, such as an increase above a threshold temperature indicative of an initiation of an autoclave process. In some examples, this threshold temperature may be determined based on a history of measuring temperatures of sterilization cases at, or shortly before or after, the initiations of autoclave processes. Operation 212 may be performed by a switching component, which may include a temperature sensor for detecting a temperature of the sterilization case.

At operation 214, the supplying of power to the tracking component is stopped (i.e., interrupted), such as based on the initiation of the first autoclave process. As described above, the supplying of power to the tracking component may be stopped by disconnecting the battery from the tracking component or otherwise preventing the flow of power from the battery to the tracking component. Operation 212 may be performed by a switching component, which may include a switch for disconnecting the battery from the tracking component or otherwise preventing the flow of power from the battery to the tracking component.

At operation 216, a completion condition is detected that is indicative of a completion of the autoclave process. In some examples, the completion condition may be a decrease in the temperature of the sterilization case, such as a decrease below a threshold temperature indicative of a completion of the autoclave process. In some examples, this threshold temperature may be determined based on a history of measuring temperatures of sterilization cases at, or shortly before or after, the completions of autoclave processes. Operation 216 may be performed by a switching component, which may include a temperature sensor for detecting a temperature of the sterilization case.

At operation 218, the supplying of power to the tracking component is resumed, such as based on the completion of the first autoclave process. As described above, the supplying of power to the tracking component may be resumed by reconnecting the battery to the tracking component or otherwise resuming the flow of power from the battery to the tracking component. Operation 218 may be performed by a switching component, which may include a switch for connecting the battery to the tracking component or otherwise resuming the flow of power from the battery to the tracking component. At operation 220, operations 212-218 may be repeated for each consecutive autoclave process.

At operation 222, the usage information that is tracked and stored by the tracking component is transmitted to an external device that is external to the sterilization case, such as a smartphone, tablet or other mobile device. As described above, the usage information may be transmitted periodically by the tracking component, such as at repeating intervals, for example every few minutes while the tracking component is powered-on. It is noted, however, that while the usage information may be transmitted periodically at repeating intervals, there may not always be an external device within range of the tracking component that has a connection to the tracking component. Thus, not all transmissions of the usage information will actually be successfully received by an external device. In some examples, the usage information may be transmitted using a short-range wireless communications protocol, such as the BLUETOOTH® protocol. As described above, the usage information may include information such as a count of autoclave processes that are performed on the sterilization case, durations of time periods between consecutive autoclave processes, and a duration of a time period between a most recent autoclave process and a time at which the usage information is obtained from the tracking component by the external device. As also described above, in some examples, after being received by the external device, the usage information may be re-transmitted to analysis services, such as cloud-based or server-based services, for further computation and analysis.

In some examples, the tracking component may detect that the usage information has been obtained by the external device, such as by having the tracking component receive a return signal from the external device that confirms receipt of the usage information by the external device. In some examples, when the tracking component detects that the usage information has been obtained by the external device, such as via receipt of the return signal from the external device, the tracking component may delete or clear the usage information that is stored in memory, thereby allowing additional space for future usage information to be written into the memory.

At operation 224, the location of the sterilization case is determined. As described above, in some examples, the location of the sterilization case may be determined based on the location of the external device when the external device obtains the user information from the tracking component. Specifically, in some examples, the external device may include location-based services, such as global positioning system (GPS) services, which may be used to determine the location of the external device. In some examples, because the tracking component and the external device may communicate via a short-range wireless communications protocol, the location of the external device may be assumed to be identical or almost identical to the location of the sterilization case. The location of the sterilization case at the time that it transmits data to the external device may therefore be determined based on the location of the external device at that same time. For example, the location of the sterilization case at the time that it transmits data to the external device may be determined to be identical or almost identical to the location of the external device at that same time.

At operation 226, a quantity of autoclave process performed on the sterilization case is determined. In some examples, this quantity may be determined based on the tracked usage information, such as by software executing on the external device and/or at the analysis services. As described above, as part of the tracked usage information for the sterilization case, the tracking component may track and store a quantity of autoclave process performed on the sterilization case. As described above, in some examples, the usage information stored by the tracking component may be deleted and overwritten each time that the usage information is successfully obtained by an external device. Thus, in some examples, the quantity of autoclave processes tracked and stored by the tracking component may be a quantity of autoclave process performed on the sterilization case since a previous time that the usage information was successfully obtained by an external device, causing the quantity count to be deleted and overwritten.

At operation 228, times of autoclave process performed on the sterilization case are determined. In some examples, these times may be determined based on the tracked usage information, such as by software executing on the external device and/or at the analysis services. For example, the usage information may include a first duration of a first time period between a completion of a most recent autoclave process and a time at which the usage information is obtained from the tracking component by an external device. In some examples, the time at which the most recent autoclave process is completed may be determined by subtracting the first duration of the first time period from the time at which the usage information is obtained. Also, in some examples, because the tracking component may be powered-off during autoclave processes, the exact times of the autoclave processes may be unknown and may instead be estimated, such based on average durations of autoclave processes that may be measured over time. An estimated autoclave process duration may then be used to estimate times of other autoclave processes preceding the most recent autoclave process. For example, a time of a completion of an autoclave process may be determined by subtracting, from the time at which the usage information is obtained, the estimated autoclave process duration for each intervening autoclave process and the measured time durations that are tracked before each intervening autoclave process and after the most recent autoclave process.

Figure 3:
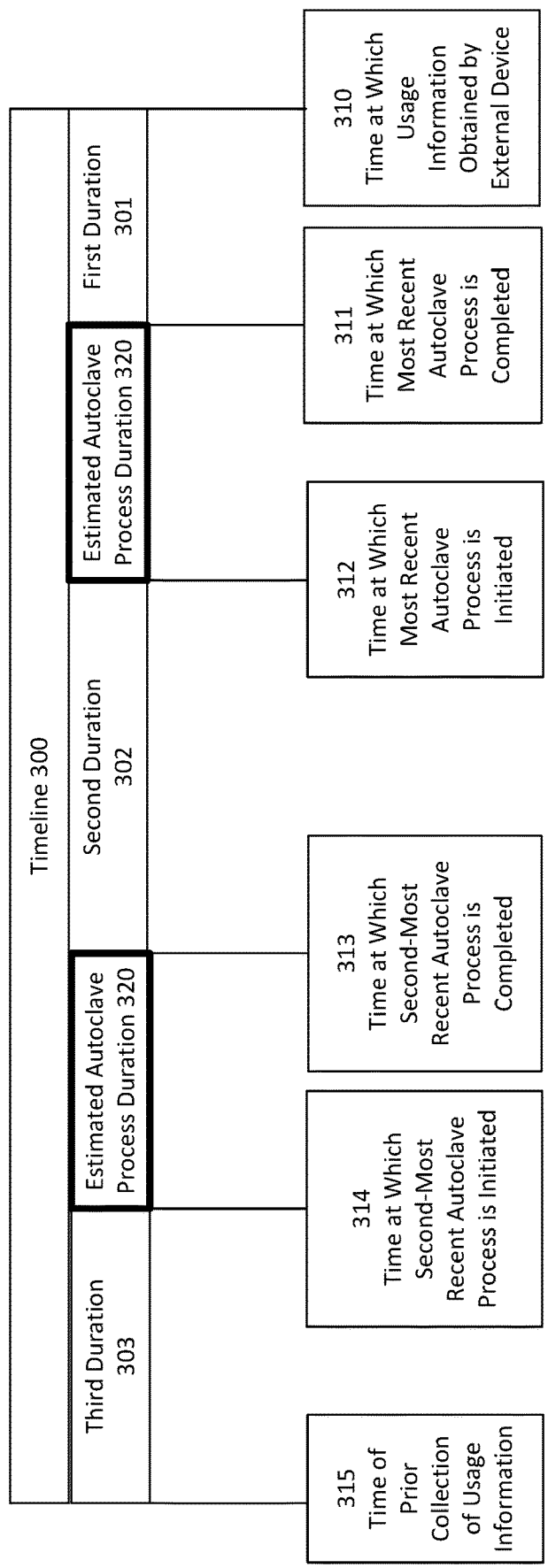
FIG. 3 is a diagram of example estimated autoclave process times based on tracked information that may be used in accordance with the present disclosure.

Referring now to FIG. 3, some examples of estimated autoclave process times that may be determined at operation 228 based on tracked information will now be described in detail. Specifically, FIG. 3 displays a timeline 300 that may be constructed based on the usage information obtained from the tracking component. The timeline 300 is oriented such that moving from right to left along the timeline 300 is a subtraction (or backward movement) in time, while moving from left to right along the timeline 300 is an addition (or forward movement) in time. As shown in FIG. 3, time 310 is a time at which the usage information is obtained (e.g., received via short-range wireless transmission) by the external device from the tracking component. Time 310 is shown on the right edge of timeline 300 because it is the most recently occurring event in the timeline 300. In some examples, the external device may include a clock or other timing component that may be used to determine the time 310 at which it obtains the usage information from the tracking component.

In the example of FIG. 3, the usage information obtained from the tracking component includes a first duration 301, a second duration 302, and a third duration 303. The first duration 301 is a duration of a first time period between the completion of the most recent autoclave process and the time 310 at which the usage information is obtained by the external device. The second duration 302 is a duration of a second time period between the completion of a second-most recent autoclave process and an initiation of the most recent autoclave process. The third duration 303 is a duration of a third time period between a time 315 of a prior collection of usage information and an initiation of the second-most recent autoclave process.

As shown in FIG. 3, a time 311 at which the most recent autoclave process is completed may be determined by subtracting (i.e., moving from right to left along timeline 300) the first duration 301 from the time 310 at which the usage information is obtained by the external device from the tracking component. As described above, the first duration 301 is included in the usage information obtained by the external device from the tracking component.

Next, a time 312 is determined at which the most recent autoclave process is initiated. As described above, in order to preserve and extend battery life, the tracking component is powered-off during autoclave cycles. Thus, the exact duration of the most recent autoclave process cannot be determined based on the usage information obtained from the tracking component. Instead, the duration of the most recent autoclave process may be estimated using an estimated autoclave process duration 320. As described above, in some examples, the estimated autoclave process duration 320 may be determined based on average durations of autoclave processes that may be measured over time. As shown in FIG. 3, the time 312 at which the most recent autoclave process is initiated may be estimated by subtracting (i.e., moving from right to left along timeline 300) the estimated autoclave process duration 320 from the time 311 at which the most recent autoclave process is completed.

Next, as shown in FIG. 3, a time 313 at which a second-most recent autoclave process is completed may be estimated by subtracting (i.e., moving from right to left along timeline 300) the second duration 302 from the estimated time 312 at which the most recent autoclave process is initiated. As described above, the second duration 302 is included in the usage information obtained by the external device from the tracking component. Thus, the time 313 at which second-most recent autoclave process is completed may be determined by subtracting the first duration 301, the second duration 302, and the estimated autoclave process duration 320 from the time 310 at which the usage information is obtained by the external device.

Next, a time 314 is estimated at which the second-most recent autoclave process is initiated. As shown in FIG. 3, the time 314 at which the second-most recent autoclave process is initiated may be estimated by subtracting (i.e., moving from right to left along timeline 300) the estimated autoclave process duration 320 from the time 313 at which the second-most recent autoclave process is completed.

It is noted that, while the above description relates to subtracting various time durations from the time 310 at which usage information is obtained by the external device, it may also be possible to determine and estimate times of autoclave processes by adding tracked time durations to the time 315 of a prior collection of usage information from the tracking component. For example, the time 314 at which the second-most recent autoclave process is initiated may be determined by adding the third duration 303 to the time 315 of the prior collection of usage information from the tracking component. The time 313 at which the second-most recent autoclave process is completed may then be estimated by adding the estimated autoclave process duration 320 to the time 314 at which the second-most recent autoclave process is initiated. The time 312 at which the most recent autoclave process is initiated may then be estimated by adding the second duration 302 to the time 313 at which the second-most recent autoclave process is completed. The time 311 at which the most recent autoclave process is completed may then be estimated by adding the estimated autoclave process duration 320 to the time 313 at which the most recent autoclave process is initiated. It is further noted that, while FIG. 3 represents an example in which two autoclave processes are performed between consecutive collections of usage data from the tracking component, any number of autoclave processes may be performed, and the time periods between those autoclave processes may be tracked, stored and reported using the techniques described above.

Example Computing Device

Figure 4:
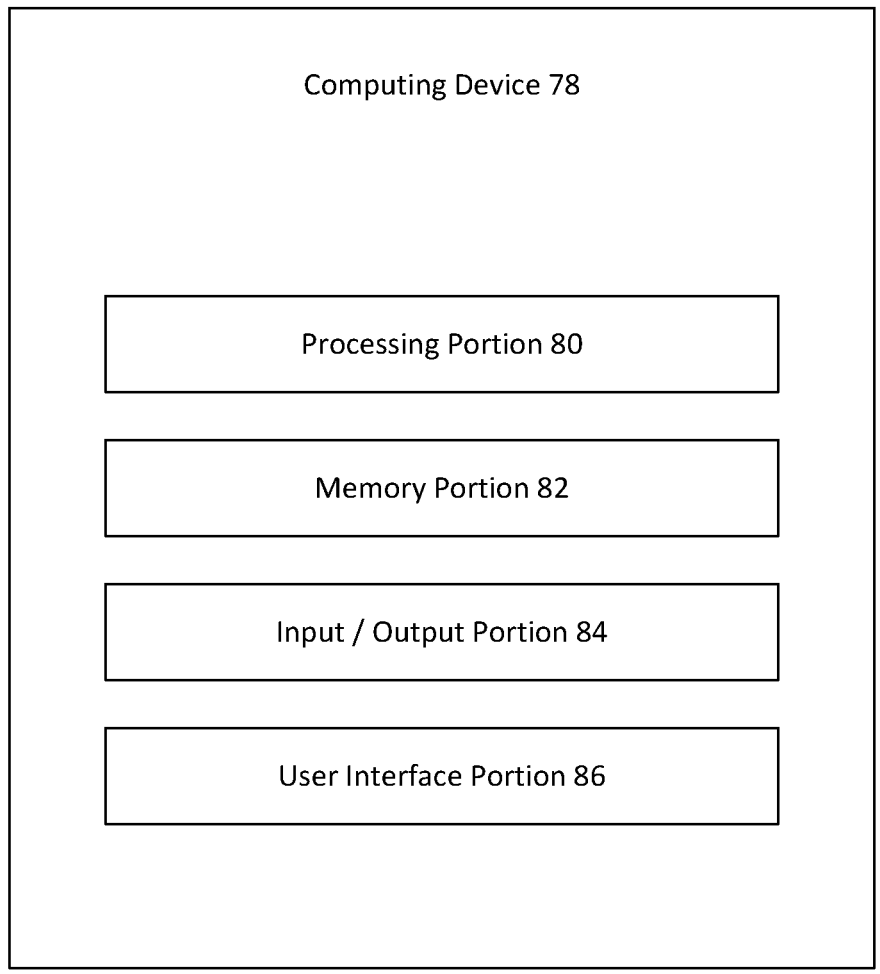
FIG. 4 is a block diagram of an example computing device for use in accordance with the present disclosure.

Referring to FIG. 4, a suitable computing device such as example computing device 78 can be configured to perform any or all of the techniques set forth above. In one specific example, external device 120 may be or may include a computing device 78. It will be understood that the computing device 78 can include any appropriate device, examples of which include a desktop computing device, a server computing device, or a portable computing device, such as a laptop, tablet, or smart phone. It is further noted that, in some examples, other components described herein, such as tracking component 113 and switching component 112, may include certain features of the computing device 78, such as processing portion 80, a memory portion 82, and an input/output portion 84. Thus, in some examples, any description of these and other features of computing device 78 may be considered to potentially apply to those and other components, even if those components may not necessarily include all features of the computing device 78.

In an example configuration, the computing device 78 includes a processing portion 80, a memory portion 82, an input/output portion 84, and a user interface (UI) portion 86. It is emphasized that the block diagram depiction of the computing device 78 is exemplary and not intended to imply a specific implementation and/or configuration. The processing portion 80, memory portion 82, input/output portion 84, and user interface portion 86 can be coupled together to allow communications therebetween. As should be appreciated, any of the above components may be distributed across one or more separate devices and/or locations.

In various embodiments, the input/output portion 84 includes a receiver of the computing device 78, a transmitter of the computing device 78, or a combination thereof. The input/output portion 84 is capable of receiving and/or providing information pertaining to communicate a network such as, for example, the Internet. As should be appreciated, transmit and receive functionality may also be provided by one or more devices external to the computing device 78.

The processing portion 80 may include one or more processors. Depending upon the exact configuration and type of processor, the memory portion 82 can be volatile (such as some types of RAM), non-volatile (such as ROM, flash memory, etc.), or a combination thereof. The computing device 78 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 78.

The computing device 78 also can contain the user interface portion 86 allowing a user to communicate with the computing device 78. The user interface 86 can include inputs that provide the ability to control the computing device 78, via, for example, buttons, soft keys, a mouse, voice actuated controls, a touch screen, movement of the computing device 78, visual cues (e.g., moving a hand in front of a camera on the computing device 78), or the like. The user interface portion 86 can provide outputs, including visual information (e.g., via a display), audio information (e.g., via speaker), mechanically (e.g., via a vibrating mechanism), or a combination thereof. In various configurations, the user interface portion 86 can include a display, one or more graphical user interfaces, a touch screen, a keyboard, a mouse, an accelerometer, a motion detector, a speaker, a microphone, a camera, a tilt sensor, or any combination thereof. Thus, a computing system including, for example, one or more computing devices 78 can include a processor, a display coupled to the processor, and a memory in communication with the processor, one or more graphical user interfaces, and various other components. The memory can have stored therein instructions that, upon execution by the processor, cause the computer system to perform operations, such as the operations described above. As used herein, the term computing system can refer to a system that includes one or more computing devices 78. For instance, the computing system can include one or more server computing devices that communicate with one or more client computing devices.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other processor-readable or machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. A system comprising:
    a sterilization case configured to store medical instruments during sterilizing of the medical instruments;
    a tracking component that is battery-powered and that is configured to collect, store and transmit one or more time parameters associated with the sterilization case, wherein the tracking component comprises a timer configured to count or measure the one or more time parameters;
    a switching component configured to perform operations comprising:
        detecting an initiation condition indicative of an initiation of a first autoclave process that sterilizes the medical instruments in the sterilization case, wherein power is supplied to the tracking component prior to the initiation of the first autoclave process;
        stopping, based on the initiation of the first autoclave process, supplying of the power to the tracking component;
        detecting a completion condition indicative of a completion of the first autoclave process; and
        resuming, based on the completion of the first autoclave process, the supplying of the power to the tracking component; and
    a computing device including:
        one or more processors; and
        memory having stored therein first instructions that, upon being executed by the one or more processors, cause the computing device to:
            determine a first complete time at which the first autoclave process is completed by subtracting a first time interval from an obtain time at which the one or more time parameters are obtained by the computing device from the tracking component, wherein the first time interval corresponds to a first time period between the completion of the first autoclave process and the obtain time at which the one or more time parameters are obtained by the computing device from the tracking component, and wherein the first time interval is included in the one or more time parameters.

2. The system of claim 1, wherein the memory has stored therein additional instructions that, upon being executed by the one or more processors, cause the computing device to:
    determine a second complete time at which a second autoclave process is completed by subtracting the first time interval, a second time interval and an estimated autoclave process duration from the obtain time at which the one or more time parameters are obtained by the computing device from the tracking component, wherein the second time interval corresponds to a second time period between the initiation of the first autoclave process and a completion of the second autoclave process, and wherein the second time interval is included in the one or more time parameters.

3. The system of claim 1, wherein the memory has stored therein additional instructions that, upon being executed by the one or more processors, cause the computing device to:
    determine a location of the sterilization case based on a location of the computing device.

4. The system of claim 1, wherein the timer is a crystal oscillator.

* * * * *